United States Patent
Phillips et al.

(10) Patent No.: US 10,953,130 B2
(45) Date of Patent: Mar. 23, 2021

(54) SOLID HEMOSTATIC COMPOSITION AND METHODS OF MAKING THE SAME

(71) Applicant: Victor Matthew Phillips, Jefferson City, MO (US)

(72) Inventors: Victor Matthew Phillips, Jefferson City, MO (US); John Garner, West Lafayette, IN (US)

(73) Assignee: Victor Matthew Phillips, Jefferson City, MO (US)

(*) Notice: Subject to any disclaimer, the term of this patent is extended or adjusted under 35 U.S.C. 154(b) by 190 days.

(21) Appl. No.: 15/692,654

(22) Filed: Aug. 31, 2017

(65) Prior Publication Data

US 2019/0060512 A1 Feb. 28, 2019

(51) Int. Cl.
| | | |
|---|---|---|
| *A61L 24/00* | (2006.01) | |
| *A61L 26/00* | (2006.01) | |
| *A61L 24/04* | (2006.01) | |
| *A61K 47/38* | (2006.01) | |
| *A61K 47/34* | (2017.01) | |
| *A61K 9/00* | (2006.01) | |
| *A61L 15/32* | (2006.01) | |
| *A61K 47/36* | (2006.01) | |
| *A61K 47/42* | (2017.01) | |
| *A61K 47/12* | (2006.01) | |
| *A61K 9/06* | (2006.01) | |

(52) U.S. Cl.
CPC ........ *A61L 24/0042* (2013.01); *A61K 9/0019* (2013.01); *A61K 9/06* (2013.01); *A61K 47/12* (2013.01); *A61K 47/34* (2013.01); *A61K 47/36* (2013.01); *A61K 47/38* (2013.01); *A61K 47/42* (2013.01); *A61L 15/32* (2013.01); *A61L 24/043* (2013.01); *A61L 26/009* (2013.01); *A61L 26/0038* (2013.01); *A61L 26/0052* (2013.01); *A61L 2400/04* (2013.01)

(58) Field of Classification Search
None
See application file for complete search history.

(56) References Cited

U.S. PATENT DOCUMENTS

| | | |
|---|---|---|
| 8,771,258 B2 | 7/2014 | Hedrich |
| 9,827,348 B2 | 11/2017 | Girdhar |
| 2003/0175327 A1 | 9/2003 | Cochrum |
| 2009/0246261 A1* | 10/2009 | Delmotte ............... A61P 7/02 424/445 |
| 2014/0220130 A1* | 8/2014 | Larsen ............... A61L 26/0066 424/484 |
| 2014/0348921 A1 | 11/2014 | Lesage |
| 2016/0206777 A1 | 7/2016 | Dowling |
| 2016/0213809 A1 | 7/2016 | Kudela |
| 2017/0035861 A1 | 2/2017 | Phillips |
| 2017/0080119 A1 | 3/2017 | Hedrich |
| 2017/0165403 A1* | 6/2017 | Cazalbou ............ A61B 17/8802 |

FOREIGN PATENT DOCUMENTS

| | | |
|---|---|---|
| WO | 2001082937 A1 | 11/2001 |
| WO | 2001097826 A2 | 12/2001 |

OTHER PUBLICATIONS

Wiggins, et al., Hydrolytic degradation of poly(D,L-lactide) as a function of end group: Carboxylic acid vs. hydroxyl, Polymer 47 (2006) 1960-69).*

* cited by examiner

Primary Examiner — H. Sarah Park
(74) Attorney, Agent, or Firm — Armstrong Teasdale LLP

(57) ABSTRACT

A solid hemostatic composition for use within a biological tissue at an internal treatment site includes a biopolymer configured to cross-link with red blood cells at the site to facilitate clot formation at the site, a first thickener that includes (hydroxypropyl)methyl cellulose (HPMC), a second thickener that includes animal-derived gelatin, and a bioadhesive that includes a low molecular weight poly (lactide).

12 Claims, No Drawings

SOLID HEMOSTATIC COMPOSITION AND METHODS OF MAKING THE SAME

BACKGROUND

The subject matter described herein relates generally to hemostatic compositions and, more particularly, to hemostatic compositions configured for introduction to a site of a surgical incision or other defect within a biological tissue.

It is necessary to inhibit bleeding from such sites, such as during and after a surgical procedure, to minimize risk to a subject. One known method to inhibit bleeding at such a site involves suturing. However, many defects within biological tissue, such as those resulting from arteriotomies, involve internal incisions that are not easily accessible by suturing instruments. Other known methods to inhibit bleeding at such a site include an application of pressure manually the use of a hemostatic device, and/or the use of absorbent materials, such as gauze and/or sponges. However, the effectiveness of such methods is limited for at least some defects within biological tissue after the procedure is complete. In addition, hemostatic compounds that include biopolymer materials such as chitosan and/or enzymatic clotting factors such as thrombin are known for treating skin wounds. However, an ability to deliver such known gel compounds to an internal site is typically limited.

BRIEF SUMMARY

In one aspect, a solid hemostatic composition for use within a biological tissue at an internal treatment site is provided. The solid hemostatic composition includes a biopolymer configured to cross-link with red blood cells at the site to facilitate clot formation at the site, a first thickener that includes (hydroxypropyl)methyl cellulose (HPMC), a second thickener that includes animal-derived gelatin, and a bioadhesive that includes a low molecular weight poly (lactide).

In another aspect, a method of making a solid hemostatic composition for use within a biological tissue at an internal treatment site is provided. The method includes mixing a biopolymer solution and one or more thickener suspensions. The biopolymer solution includes a biopolymer dissolved in a first solvent, and each of the one or more thickener suspensions includes a respective thickener suspended in a liquid medium. The method also includes drying the mixture of the biopolymer solution and the one or more thickener suspensions such that a dried mixture of the biopolymer and the one or more thickeners is formed, and adding a bioadhesive solution to the dried mixture of the biopolymer and the one or more thickeners such that a mixture of the bioadhesive solution, the biopolymer, and the one or more thickeners is formed. The method further includes drying the mixture of the bioadhesive solution, the biopolymer, and the one or more thickeners to form the solid hemostatic composition.

DETAILED DESCRIPTION

The compositions and methods described herein relate to the inhibition of blood loss from a surgical incision or other defect within a biological tissue of a subject and, more particularly, to a solid hemostatic composition for inhibiting internal blood flow from a subject and methods of making the solid hemostatic composition. In some embodiments, the hemostatic composition is delivered in a substantially solid state and absorbs bodily fluids at the treatment site, expands, and occludes an incision or other defect in the biological tissue to prevent blood loss. For example, but not by way of limitation, the hemostatic composition is deliverable to the treatment site using a device of the type described in U.S. Pat. No. 9,642,604, of the type described in U.S. Pat. No. 9,724,081, or of the type described in U.S. patent application Ser. No. 14/708,943 filed May 11, 2015, all of which are hereby incorporated by reference in their entirety.

The hemostatic composition is formed by combining a biopolymer solution that includes a hemostatic biopolymer dissolved in a first solvent, and one or more thickener suspensions that each include a respective thickener suspended in a liquid medium. A bioadhesive is added to the combination, and the combined biopolymer, thickener, and bioadhesive mixture is dried to form the solid hemostatic composition. In some embodiments, an initial mixture of the biopolymer solution and the one or more thickener suspensions is allowed to dry, and the bioadhesive is provided via a bioadhesive solution that includes the bioadhesive dissolved in a second solvent. More specifically, the bioadhesive solution is added to the initially dried biopolymer and thickener mixture, and the resulting mixture is again dried to form the solid hemostatic composition. Alternatively, the bioadhesive is provided by pre-dissolving it into the biopolymer solution and/or the one or more thickener suspensions, or by adding the separate bioadhesive solution to the mixture of the biopolymer solution and the one or more thickener suspensions prior to initial drying.

In certain embodiments, a flat portion of the dried, solidified hemostatic composition is peeled from a drying surface, cut into a substantially rectangular shape, and rolled into a thin-walled tubular shape for delivery to the internal treatment site. Alternatively, in some embodiments, the dried biopolymer and thickener mixture is ground into a powder. In some such embodiments, the powder is further shaped into a delivery unit for delivery to the treatment site. Alternatively, the hemostatic composition is delivered to the treatment site in powdered form.

By way of non-limiting example, the thickener includes at least one of animal-derived gelatin and (hydroxypropyl) methyl cellulose (HPMC). In some embodiments, the thickener is formed from a combination of multiple types of materials, and an amount of each of the thickener materials is selected, in combination with amounts of the biopolymer and a bioadhesive, to facilitate balancing an expansion ratio of the hemostatic composition in response to fluid absorption with a bioadhesion of the expanded hemostatic composition in situ.

In some aspects, the hemostatic composition further includes a hardener that interacts with the hemostatic biopolymer to enhance the occlusion and/or strength of the hemostatic composition after application. By way of a non-limiting example, the hardener includes glutaraldehyde added in liquid form to the combined biopolymer and thickener mixture prior to drying. Alternatively, the hemostatic composition does not include a hardener.

In some aspects, the hemostatic composition further includes at least one additional active agent. By way of non-limiting example, the at least one additional active agent is provided by pre-dissolving it into the biopolymer solution or the thickener suspension. By way of another non-limiting example, the at least one additional active agent is provided by adding a solution including the additional active agent to the previously formed dried biopolymer and thickener mixture, and re-drying the mixture to form the hemostatic composition. For example, the at least one additional active agent is released in active form from the hemostatic composition in situ to further facilitate healing at the site. In some embodiments, the at least one additional active agent includes a clotting agent, such as, but not limited to, thrombin. Additionally or alternatively, the at least one active agent is selected to provide an additional benefit, including but not limited to, preventing infection or otherwise accelerating healing. Alternatively, the hemostatic composition does not include any additional active agent.

For example, but not by way of limitation, the defect within biological tissue at the internal treatment site is associated with a medical procedure, such as, but not limited to, general surgery, thoracic/pulmonary surgery, colon resection, hepatobiliary surgery, pancreatic surgery, gynecologic surgery, orthopedic surgery, trauma surgery, ear-nose-throat (ENT) surgery, cosmetic surgery, urological procedures, neurosurgery, and cardiovascular surgery. In some embodiments, the defect is one or more suture lines created in a surgical procedure including, but not limited to, aortic root repair, aortic arch repair, aortotomy, aortic reconstruction, CABG, LVAD implantation, carotid endarterectomy, abdominal aortic aneurysm repair, and femoral bypass (fem-fem bypass or fem-pop bypass).

After introduction of the composition to the internal treatment site, using any suitable method including, but not limited to, injection, the composition absorbs bodily fluids at the site, which causes the composition to expand and, thus, to occlude the treatment site and inhibit blood loss from the incision or other defect. The tendency of the solid hemostatic composition to expand at the internal treatment site in response to absorption of bodily fluids facilitates use of a relatively small initial volume of the hemostatic composition, enabling internal delivery to the surgical incision or other defect through a small diameter passage from the outer skin, such as a passage initially formed by a catheter used for a preceding medical procedure. Moreover, in some embodiments, the biopolymer of the hemostatic composition rapidly cross-links with biological cells the site to facilitate occlusion at the site, and the bioadhesive further facilitates inhibition of blood loss from the site by enhancing adhesion of the hemostatic composition to the tissues surrounding the site.

In an aspect, the hemostatic composition safely biodegrades in vivo as the incision or other defect heals, eliminating a need for any secondary removal process.

In various aspects, the hemostatic composition is formulated to enable at least one property such as, but not limited to, expandability of the solid hemostatic composition in situ at the internal treatment site; bioadhesiveness of the hemostatic composition to the tissues surrounding the surgical incision or other defect; hemostatic properties of the hemostatic composition; occlusiveness of the hemostatic composition after expansion; suitability of the hemostatic composition for certain surgical methods and/or injection devices; and any other relevant property. The properties of the hemostatic composition are influenced by one or more of several factors including, but not limited to, the composition of the biopolymer solution; the amount and properties of the material(s) used as the one or more thickeners; the composition of the bioadhesive solution; the properties of the at least one additional active agent; the selected method of introducing the hemostatic composition to the internal treatment site; and any other relevant property.

In certain embodiments, the biopolymer includes at least one polycationic polymer. Without being limited to any particular theory, the cationic charges distributed within the polycationic polymer impart bioadhesive properties to enable the binding of a hemostatic composition containing the polycationic polymers to negatively charged surfaces including, but not limited to, biological tissues in the vicinity of a site of a biological defect. Thus, after introduction to the site, the polycationic biopolymers cross-link with negatively charged red blood cells at the site of the biological defect to further link the hemostatic composition to the biological tissues proximate the site. Non-limiting examples of polycationic polymers suitable for inclusion in the biopolymer solution include: chitosan, chitin, diethylaminoethyl-dextran, diethylaminoethyl-cellulose, diethylaminoethyl-agarose, diethylaminoethyl-alginate, any other polymer modified with a diethylaminoethyl group, any polymer containing a plurality of protonated amino groups, any polypeptide having an average residue isoelectric point above about 7, and any combination thereof.

In some embodiments, chitosan is selected as the polycationic polymer. Chitosan, as used herein, describes a naturally occurring linear polysaccharide composed of randomly distributed β-(1-4)-2-amino-2-D-glucosamine (deacetylated) and β-(1-4)-2-acetamido-2-D-glucoseamine (acetylated) units. Chitosan may be derived from chitin, a naturally occurring polymer isolated from fungi, from mollusks, or from the exoskeletons of arthropods (e.g., crustaceans and insects). In one embodiment, the chitosan is produced by subjecting chitin to a process of alkaline deacetylation. As described more generally above, without being limited to any particular theory, the positive charge (cationic) distribution along the backbone of the chitosan interact electrostatically with negatively charged biological cells, thus creating a sticky interface or electrostatic attraction between the chitosan within the hemostatic composition and biological tissues proximate the site. In addition, chitosan is also known to possess inherent anti-microbial properties.

In certain embodiments, the chitosan is produced using an alkaline deacetylation of chitin using a strong alkaline solution according to known methods. Typically, any chitin-based biopolymer with a degree of deacetylation greater than about 50% is referred to as chitosan. The degree of deacetylation of the chitosan may influence the characteristics of the hemostatic composition in which the chitosan is included. Non-limiting examples of characteristics of the hemostatic composition that may be influenced by the degree of acetylation of the chitosan include bioadhesive properties, and resistance to premature degradation in vivo at the surgical site.

In various embodiments, the chitosan is provided in any suitable form including, but not limited to, a powder, coarse ground flakes, or dissolved in a weak acid solvent. In some embodiments, the molecular weight of the chitosan is ranges from about 60 kDaltons to about 375 kDaltons (viscosity-average molecular weight $M_v$). Without being limited to any particular theory, the inclusion of chitosan of relatively higher molecular weight, such as at least 150 kDaltons, results in relatively slower degradation in vivo.

Without being limited to any particular theory, chitosan is degraded in vivo by, for example, lysozyme, N-acetyl-o-glucosaminidase, and lipases, and the byproducts of chitosan degradation are saccharides and glucosamines that are gradually absorbed by the body. Therefore, no secondary process for removal of chitosan from the body is required. Chitosan compositions having a 50% degree of deacetylation are known to be highly degradable in vivo. As the degree of deacetylation increases, chitosan typically becomes increasingly resistant to degradation. Chitosan compositions having a degree of deacetylation that is higher than 95% degrade slowly over weeks or months. In certain embodiments, the degree of deacetylation of the chitosan in the biopolymer solution ranges from about 50% to about 100%. Moreover, in some embodiments, the degree of deacetylation ranges from about 50% to about 80%. Moreover, in certain embodiments, the degree of deacetylation ranges from about 65% to about 80%. In particular embodiments, the degree of deacetylation of the chitosan in the biopolymer solution is about 75%.

In certain embodiments, the first solvent of the biopolymer solution is a dilute acid solution, including but not limited to, an aqueous solution that includes at least one of acetic, citric, oxalic, proprionic, ascorbic, hydrochloric, formic, lactic, or any other suitable organic or inorganic acid, at a concentration ranging from about 0.1% to about 5% (v/v). By way of non-limiting example, the at least one polycationic polymer selected as the biopolymer is substantially insoluble in water and organic solvents, but is fairly soluble in dilute acid solutions. In some embodiments, the dilute acid is selected to influence at least one property of the hemostatic composition including, but not limited to, susceptibility to degradation in vivo. Additionally or alternatively, a concentration of the dilute acid and/or a time period over which the chitosan is dissolved in the dilute acid is selected to influence at least one property of the hemostatic composition, including, but not limited to, susceptibility to degradation in vivo. In one embodiment, the dilute acid is 1% L-lactic acid (v/v). In another embodiment, the dilute acid is 1% acetic acid (v/v).

In some embodiments, the selected concentration of the biopolymer dissolved in the first solvent enables delivery of an effective amount of the biopolymer while maintaining an ability to suitably dry the mixture of the biopolymer solution and the one or more thickener suspensions. In some embodiments, the biopolymer solution includes about 1% to about 3% w/v of chitosan of a relatively high molecular weight, as described above, dissolved in 1% acetic acid. In some such embodiments, the biopolymer solution includes about 2% w/v chitosan of a relatively high molecular weight dissolved in 1% acetic acid. For another example, the biopolymer solution includes from about 1% to about 3% w/v of chitosan of a relatively high molecular weight dissolved in 1% L-lactic acid. In certain embodiments, the strength of the acid has a pH of at least about 4. In particular embodiments, the strength of the acid is selected to result in a pH of at least about 2.

As noted above, in some embodiments, the one or more thickeners include at least one of animal-derived gelatin and HPMC. By way of non-limiting example, the animal-derived gelatin is derived from bovine skin. In alternative embodiments, the one or more thickeners include any suitable material or combination of materials that enables the hemostatic composition to function as described herein. In some embodiments, each of a plurality of thickener materials of the thickener is provided in a separate thickener suspension, and the separately provided thickener suspensions are each mixed with the biopolymer solution. As noted above, in some such embodiments, the combination of thickener materials facilitates balancing an expansion ratio of the hemostatic composition in response to fluid absorption with a bioadhesion of the expanded hemostatic composition in situ.

In certain embodiments, the liquid medium of the one or more thickener suspensions is deionized water (DiH20). In alternative embodiments, the liquid medium is any suitable material or combination of materials that enables the hemostatic composition to function as described herein. Moreover, although embodiments described herein include first and second thickener suspensions in an identical liquid medium, in alternative embodiments, the liquid medium includes a different liquid medium for each thickener suspension. In certain embodiments, the selected concentrations of each of the one or more thickeners suspended in the liquid medium enable delivery of an effective amount of the thickener while maintaining an ability to suitably dry a mixture of the biopolymer solution and the one or more thickener suspensions. In some embodiments, a first thickener suspension includes about 1% to about 5% w/v of HPMC suspended in DiH20, and a second thickener suspension includes about 1% to about 10% w/v of gelatin suspended in DiH20. In some such embodiments, the first thickener suspension includes about 1% to about 3% w/v of HPMC suspended in DiH20, and the second thickener suspension includes about 3% to about 7% w/v of gelatin suspended in DiH20. Moreover, in one embodiment, the first thickener suspension includes about 2% w/v of HPMC suspended in DiH20, and the second thickener suspension includes about 5% w/v of gelatin suspended in DiH20.

In some embodiments, the bioadhesive includes a biodegradable polymer. For example, the bioadhesive is a low molecular weight polymer, such as but not limited to a poly(lactide). In one such embodiment, the bioadhesive is an acid-terminated poly(D,L-lactide) having a molecular weight ranging from about 1,000 Dalton to about 5,000 Dalton. In some embodiments, the bioadhesive implemented as a low molecular weight poly(lactide) unexpectedly improves bioadhesion, as compared to bioadhesives including polyacrylic acids and other ionically charged polymers. In alternative embodiments, the bioadhesive is any suitable material, including polyacrylic acids and other ionically charged polymers, that enables the hemostatic composition to function as described herein.

In certain embodiments, the second solvent in which the bioadhesive solution is provided is acetonitrile. In alternative embodiments, the second solvent is any suitable material or combination of materials that enables the hemostatic composition to function as described herein. In some embodiments, the selected concentration of the bioadhesive in the bioadhesive solution enables delivery of an effective amount of the bioadhesive to, as well as suitable coating of, a dried mixture of the biopolymer and the one or more thickeners obtained from allowing the mixture of the biopolymer solution and the one or more thickener suspensions to dry. Moreover, in some embodiments, the selected concentration of the bioadhesive in the bioadhesive solution enables suitable drying of the mixture of the bioadhesive solution with the dried biopolymer and one or more thickeners. It should be understood that the term "solid" hemostatic composition merely indicates that sufficient liquid is lost from the mixture to result in a solid-phase composition which does not flow like a liquid. For example, the term "solid" does not require substantially all liquid to be removed from the hemostatic composition, but rather includes, without limitation, hemostatic compositions that retain some amount of liquid in a gelled structure.

In some embodiments, the bioadhesive solution includes an acid-terminated poly(D,L-lactide) having a molecular weight ranging from about 1,000 Dalton to about 5,000 Dalton dissolved in acetonitrile at a concentration ranging from about 1% (w/v) to about 3% (w/v). In one embodiment, the bioadhesive solution includes an acid-terminated poly (D,L-lactide) having a molecular weight ranging from about 1,000 Dalton to about 5,000 Dalton dissolved in acetonitrile at a concentration of about 2% (w/v). In alternative embodiments, the bioadhesive is incorporated into the hemostatic composition in any suitable fashion. For example, the bioadhesive is dissolved directly into one or more of the biopolymer solution and the thickener suspension prior to mixture of the biopolymer solution and the one or more thickener solutions, or the bioadhesive solution is added to the mixture of the biopolymer solution and the one or more thickener solutions prior to drying of the mixture.

In some embodiments, the amounts of the biopolymer, thickener, and bioadhesive in the hemostatic composition are selected to produce both an advantageous expansion ratio of the hemostatic composition at the treatment site in response to fluid absorption, and an advantageous bioadhesion of the expanded hemostatic composition in situ. For example, in certain embodiments, with reference to the embodiments of concentrations of the biopolymer solution and the one or more thickener suspensions described above, the mixture of the biopolymer solution and the one or more thickener suspensions includes a first thickener suspension, including HPMC as the thickener, at a volume ranging from about 1.5 to 2.5 times a volume of a second thickener suspension, including animal-derived gelatin as the thickener, with a combined volume of the first and second thickener suspensions ranging from about six times to about nine times a volume of the biopolymer solution. Moreover, with reference to the embodiments of concentrations of the bioadhesive solution described above, after drying of the mixture of the biopolymer solution and the thickener solutions, the bioadhesive solution is added to the dried mixture at a volume ranging from about 20% to about 33% of the original combined volume of the one or more thickener suspensions. The solid hemostatic compositions formed from such mixtures demonstrate a swelling, in response to fluid absorption over a time period of about ten minutes, ranging from about 5 times to about 8 times an initial dried mass of the hemostatic composition at deployment. In addition, the solid hemostatic compositions formed from such mixtures, applied at an internal treatment site, demonstrate a force of bioadhesion to tissues surrounding the treatment site of at least about 0.15 Newtons, and a peel energy of at least about 0.20 Joules (i.e., the energy required to peel the delivered hemostatic composition away from the surrounding tissues). Thus, the hemostatic compositions described herein provide reliable occlusion of, and adherence to, the incision or other defect, followed by biodegradation after the site has healed.

In one such embodiment, the mixture of the biopolymer solution and the one or more thickener suspensions includes about 10 parts of the first thickener suspension including HPMC, about 5 parts of the second thickener suspension including animal-derived gelatin, and about 2 parts of the biopolymer solution, and the bioadhesive solution is added to the dried mixture of the biopolymer solution and thickener suspensions at about 4 parts (relative to original volumes of the other components). After re-drying of the mixture, the solid hemostatic composition demonstrates a swelling in response to fluid absorption ranging from about 5 times to about 6 times the initial dried mass of the hemostatic composition at deployment, an average force of bioadhesion to tissues surrounding the internal treatment site of about 0.23 Newtons, and an average peel energy of about 0.25 Joules.

In some embodiments, as noted above, the hemostatic composition includes a hardener to facilitate increasing a mechanical strength of the in situ hemostatic composition. For example, the hardener is selected for its capability to cross-link the biopolymer of the biopolymer solution into a three-dimensional matrix of interconnected, linear, polymeric chains over the defect within the biological tissue. In certain embodiments, the hardener is selected based upon at least one of the type of the polycationic polymer in the biopolymer solution, the desired degree or extent of cross-linking, biocompatibility, and any other suitable factor. Non-limiting examples of suitable crosslinking agents include sodium tripolyphosphate (NaTPP), ethylene glycol diglycidyl ether, ethylene oxide, glutaraldehyde, epichlorohydrin, diisocyanate, calcium chloride, and genipin. For example, in one embodiment, the hardener is glutaraldehyde added to the combined biopolymer solution and one or more thickener suspensions, prior to drying, at about 15 microliters per milliliter of the combined biopolymer solution and one or more thickener suspensions. In alternative embodiments, no hardener is used to form the hemostatic composition.

In some embodiments, as noted above, the at least one additional active agent includes at least one clotting agent. Without being limited to any particular theory, the at least one additional active agent is incorporated into the hemostatic composition such that it is released from the resulting clot in a predetermined release profile. Non-limiting examples of clotting agents suitable for inclusion in the hemostatic biopolymer composition include thrombin, fibrinogen, and any combination thereof. As used herein, "U" refers to an NIH-defined activity unit that corresponds to about 0.324 µg of enzymatically active thrombin. In one aspect, the hemostatic composition includes an amount of thrombin in a range from about 0.5 U to about 200 U per gram of chitosan in the biopolymer solution. In another aspect, the biopolymer solution includes an amount of thrombin in a range from about 2 U to about 160 U per gram of chitosan in the biopolymer solution.

The at least one clotting agent is incorporated into the hemostatic composition in any suitable fashion. Certain clotting agents, such as, but not limited to, thrombin, include protein-based enzymes subject to denaturing or damage that reduce a capability to perform enzymatic activity. In certain embodiments, the hemostatic composition is formulated to maintain the clotting agent in an enzymatically active state. In one aspect, the ingredients of the hemostatic composition may be selected to maintain parameters within suitable ranges to facilitate maintaining the clotting agent in an enzymatically active state. Non-limiting examples of parameters associated with maintaining the clotting agent in an enzymatically active condition include pH of the solution, ionic concentrations in the solution, temperature, and any other relevant parameter.

In certain embodiments, the at least one active agent is provided dissolved in a third solvent as an agent solution. A selected concentration of the at least one active agent in the agent solution enables delivery of an effective amount of the at least one active agent to, as well as suitable coating of, a dried mixture of the biopolymer solution and the one or more thickener suspensions. For example, thrombin as the at least one active agent is provided in a phosphate buffered saline (PBS) solution at a concentration of about 2 units per 6 milliliters of PBS, and the 6 milliliters of solution is added to about 50 milligrams of dried, powdered mixture of the biopolymer solution and thickener suspension. The hemostatic composition that maintains thrombin enzymatic activity substantially at levels associated with active uncombined thrombin. In alternative embodiments, the at least one active agent is added in any suitable fashion that enables the hemostatic composition to function as described herein. In other alternative embodiments, no additional active agent is included in the hemostatic composition.

A predetermined release profile of the at least one active agent from the hemostatic composition after introduction to the site is any suitable release profile without limitation. In certain embodiments, the predetermined release profile is influenced by at least one factor such as, but not limited to, an amount of the at least one active agent loaded in the hemostatic composition, and the manner of forming the hemostatic composition. In some embodiments, the at least one active agent is released at a relatively steady (zero-order) rate. In other embodiments, the release profile is characterized by an initial release of the at least one active agent at a relatively high rate, followed by an extended release at a relatively lower steady rate.

EXAMPLES

The following experiments were conducted to assess occlusion, mechanical strength, and deployability of embodiments of the hemostatic composition.

Initial samples of the hemostatic composition were made using 2% medium molecular weight chitosan (Aldrich catalog no. 448877) in 1% acetic acid as the biopolymer solution, 5% w/v gelatin derived from bovine skin (Aldrich catalog no. G6650) in DiH2O as a first thickener suspension, and 2% w/v HPMC (Aldrich catalog no. H-3785) in DiH2O as a second thickener suspension. The components were pipetted into paraffin-coated petri dishes each measuring 60×15 millimeters, which were gently shaken to mix and left to dry under ambient conditions overnight. The bioadhesive solution provided as 2% acid-terminated Poly(D,L-lactide) having a nominal molecular weight range of 1,000-5,000 Dalton (Akina catalog no. AP005) in acetonitrile was then pipetted into the petri dishes containing the dried mixture of biopolymer and thickener, with the exception of Sample D, and the dishes were gently shaken to mix and left to dry under ambient conditions for three days. The dried films of solidified hemostatic composition were then peeled off and tested as indicated. For Sample D, the dried mixture of biopolymer and thickener was removed first, and then dip-coated in the bioadhesive solution and hung up to dry under ambient conditions for three days.

TABLE 1

Hemostatic compositions tested.

| Sample | Description | Note |
|---|---|---|
| A | 5 mL 2% w/v HPMC<br>2.5 mL 2% w/v Chitosan<br>1 mL 5% w/v Gelatin<br>(dry overnight)<br>2 mL 2% PDLA acid endcap, 1000-5000Da,<br>in acetonitrile<br>(left to dry) | Used for deployment test,<br>successfully deployed |
| B | 5 mL 2% w/v HPMC<br>2.5 mL 2% w/v Chitosan<br>1 mL 5% w/v Gelatin<br>(dry overnight)<br>2 mL 2% PDLA acid endcap, 1000-5000Da,<br>in acetonitrile<br>(left to dry) | Used for tensile test |
| C | 5 mL 2% w/v HPMC<br>2.5 mL 2% w/v Chitosan<br>1 mL 5% w/v Gelatin<br>(dry overnight)<br>2 mL 2% PDLA acid endcap, 1000-5000Da,<br>in acetonitrile<br>(left to dry) | Used for tensile test |
| D | 5 mL 2% w/v HPMC<br>2.5 mL 2% w/v Chitosan<br>1 mL 5% w/v Gelatin<br>(dry overnight)<br>2% PDLA acid endcap, 1000-5000Da, in<br>acetonitrile<br>(dip coated and hung out to dry) | Used for deployment test,<br>successfully deployed |
| E | 5 mL 2% w/v HPMC<br>2.5 mL 2% w/v Chitosan<br>1 mL 5% w/v Gelatin<br>(dry overnight) | Control sample (no<br>bioadhesive) |
| F | 5 mL 2% w/v HPMC<br>2.5 mL 2% w/v Chitosan<br>1 mL 5% w/v Gelatin<br>(dry overnight)<br>2 mL 2% PDLA acid endcap, 1000-5000Da,<br>in acetonitrile<br>(left to dry) | Used for tensile test |

For occlusion testing, polydimethylsiloxane (PDMS, Sylgard 184) was utilized as a proxy for biological tissue. PDMS has a texture that is close to that of flesh, and PDMS is transparent so visualization is facilitated. The PDMS was crosslinked according to manufacturer instructions and cured at a depth of 1 centimeter. Squares of the PDMS were cut out and a 2 millimeter biopsy punch was used to make a hole in the center of each PDMS square. Hemostatic composition samples A and D were cut in 1×1.5 centimeter rectangular pieces and rolled into a thin-walled tubular shape for loading around a cylindrical member of a pusher of the type disclosed in U.S. Pat. No. 9,724,081. These solid thin-walled tubular samples were then deployed substantially coaxially into the PDMS holes using the pusher. The PDMS squares were then placed in 10 mL of phosphate buffered saline (PBS) as a proxy for bodily fluids and allowed to swell, expanding inward into a cylindrical shape that occluded the hole in the PDMS. Images were taken before and after the swell test using an Olympus DP70 digital camera. All of the hemostatic composition pieces were successfully deployed by the pusher into the respective PDMS hole, and all of the hemostatic composition pieces fully occluded the respective hole, each expanding between 5 and 8 times an initial dry mass of the piece over a ten minute time period. Furthermore, none of the hemostatic composition pieces came loose during the swelling process.

For mechanical testing, dog-bone shaped portions of samples B, C, and F were cut and their cross-sectional areas were measured with digital calipers. Each dog bone was loaded into the tensile clamps of a TA.XT Plus Texture Analyzer from Texture Technologies Corporation of Hamilton, Mass. Samples were tested dry. The clamps were extended at a cross-head speed of 1 millimeter per second until either 5 kilograms of force was applied, or rupture occurred. The slope of the stress-strain curve for 0-2% strain was measured as the elastic modulus. The applied stress (Pa) at rupture was taken as the tensile strength and the strain at rupture (%) was taken as maximal elongation. Table 2 shows the values for the elastic modulus, displayed as averages±standard deviation (number of trials), and are compared to a control sample E that did not include the bioadhesive. The results indicate that the presence of a low molecular weight poly(lactide) bioadhesive had no statistically significant impact on the overall elastic modulus, further confirming that the solid hemostatic composition should withstand routine handling, loading, and deployment operations.

TABLE 2

Elastic Modulus of solid hemostatic compositions.

| Samples | Elastic Modulus (MPa) |
| --- | --- |
| B, C, F | 11.53 ± 4.00 (n = 8) |
| E (control) | 11.10 ± 2.92 (n = 3) |

In addition, substantially identical samples of the hemostatic composition were tested for bioadhesion using, as a proxy for internal human tissues, freshly obtained, minimally processed pork-loin. More specifically, the solid hemostatic composition was sandwiched between two pieces of pork, with the pork-to-pork adhesion taken as representative of the tissue-to-tissue adhesion involved with using the hemostatic composition at the site of a surgical incision or other defect. One piece of pork was retained between two plastic pieces mounted on the platform of the tensile test instrument, with a pork access opening extending through one of the plastic pieces. A hook with a screw end was coupled to the other piece of pork, which was sized to fit through the access opening and clamped on the top tensile grip of the tensile test instrument to, effectively, make a pork probe. PBS was added at the adhesion site to simulate bodily fluids. After the pork pieces were briefly held in contact at the site of the hemostatic composition, the probe was retracted at a speed of 0.5 millimeters per second and the pulling force on the probe due to adhesion was measured until separation. This hemostatic composition formed by the recipe of samples A, B, C, and F in Table 1 had an average bioadhesional maximum force of 0.234±0.050 (n=3) Newtons and required 0.252±0.032 (n=3) Joules of sustained work to peel away from the representative tissue. Notably, this exceeds the bioadhesional performance of some embodiments that included polyacrylic acid and other ionically charged polymers as the bioadhesive.

Embodiments of a solid hemostatic composition and methods of making the solid hemostatic composition are described above. The embodiments provide advantages over at least some known methods of achieving hemostasis at an internal treatment site. Specifically, the amounts of the biopolymer, thickener, and bioadhesive in the solid hemostatic composition are selected to produce both an advantageous expansion ratio of the hemostatic composition at the treatment site in response to fluid absorption, and an advantageous bioadhesion of the expanded hemostatic composition in situ. For example, some embodiments provide a solid hemostatic composition that swells in response to fluid absorption from about 5 times to about 8 times the initial dried mass of the hemostatic composition at deployment, while providing a force of bioadhesion to tissues surrounding the internal treatment site of at least about 0.15 Newtons and a peel energy of at least about 0.20 Joules. Also specifically, the embodiments provide a solid hemostatic composition that can be peeled from a drying surface, cut into substantially rectangular shapes, and rolled into thin-walled tubular shapes for delivery to the internal treatment site, or alternatively ground into powdered form for delivery.

Exemplary embodiments of a hemostatic gel composition and methods of use are described above in detail. The methods and compositions are not limited to the specific embodiments described herein, but rather, steps of the methods and elements of the compositions may be utilized independently and separately from other steps and/or elements described herein. For example, the methods and compositions described herein may have other applications and are not limited to practice in association with the medical procedures as described herein. Rather, one or more embodiments may be implemented and utilized in connection with other medical applications.

As used herein, an element or step recited in the singular and proceeded with the word "a" or "an" should be understood as not excluding plural said elements or steps, unless such exclusion is explicitly stated. Further, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to illustrate the disclosure, including the best mode, and also to enable any person skilled in the art to practice the disclosure, including making and using any compositions and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A solid hemostatic composition for use within a biological tissue at an internal treatment site, said solid hemostatic composition consisting of a substantially homogeneous dried powder and comprising:
    a biopolymer configured to cross-link with red blood cells at the site to facilitate clot formation at the site wherein said biopolymer comprises chitosan;
    a first thickener comprising (hydroxypropyl)methyl cellulose (HPMC);
    a second thickener comprising animal-derived gelatin; and
    a bioadhesive comprising a poly(lactide) having a molecular weight in a range from 1,000 Dalton to about 5,000 Dalton.

2. The solid hemostatic composition of claim 1, wherein said bioadhesive comprises a biodegradable polymer.

3. The solid hemostatic composition of claim 2, wherein said bioadhesive comprises an acid-terminated poly(D,L-lactide) having a molecular weight ranging from about 1,000 Dalton to about 5,000 Dalton.

4. The solid hemostatic composition of claim 1, wherein said animal-derived gelatin is derived from bovine skin.

5. The solid hemostatic composition of claim 1, wherein an amount of said bioadhesive is sufficient to develop a bioadhesional force to tissues surrounding the internal treatment site of at least about 0.15 Newtons.

6. The solid hemostatic composition of claim 1, wherein an amount of said bioadhesive is sufficient to adhere to tissues surrounding the internal treatment site with a peel energy of at least about 0.20 Joules.

7. A solid hemostatic composition for use within a biological tissue at an internal treatment site, said solid hemostatic composition consisting of a substantially homogeneous dried material rolled into a tubular shape, the dried material comprising:
    a biopolymer configured to cross-link with red blood cells at the site to facilitate clot formation at the site wherein said biopolymer comprises chitosan;
    a first thickener comprising (hydroxypropyl)methyl cellulose (HPMC);
    a second thickener comprising animal-derived gelatin; and
    a bioadhesive comprising a poly(lactide) having a molecular weight in a range from 1,000 Dalton to about 5,000 Dalton.

8. The solid hemostatic composition of claim 7, wherein said bioadhesive comprises a biodegradable polymer.

9. The solid hemostatic composition of claim 8, wherein said bioadhesive comprises an acid-terminated poly(D,L-lactide) having a molecular weight ranging from about 1,000 Dalton to about 5,000 Dalton.

10. The solid hemostatic composition of claim 7, wherein said animal-derived gelatin is derived from bovine skin.

11. The solid hemostatic composition of claim 7, wherein an amount of said bioadhesive is sufficient to develop a bioadhesional force to tissues surrounding the internal treatment site of at least about 0.15 Newtons.

12. The solid hemostatic composition of claim 7, wherein an amount of said bioadhesive is sufficient to adhere to tissues surrounding the internal treatment site with a peel energy of at least about 0.20 Joules.

* * * * *